United States Patent [19]

Gross

[11] Patent Number: 5,704,520
[45] Date of Patent: Jan. 6, 1998

[54] LIQUID MATERIAL DISPENSER AND VALVE

[75] Inventor: Joseph Gross, Dublin, Ireland

[73] Assignee: Elan Medical Technologies, Limited, Athlone, Ireland

[21] Appl. No.: 591,583

[22] PCT Filed: Jul. 15, 1994

[86] PCT No.: PCT/IE94/00037

§ 371 Date: Mar. 27, 1996

§ 102(e) Date: Mar. 27, 1996

[87] PCT Pub. No.: WO95/03078

PCT Pub. Date: Feb. 2, 1995

[30] Foreign Application Priority Data

Jul. 19, 1993 [IE] Ireland ..................... 930532

[51] Int. Cl.$^6$ ................................. A61M 37/00
[52] U.S. Cl. ...................... 222/334; 604/141; 604/145; 417/379; 417/395
[58] Field of Search ................. 222/334; 604/141, 604/143, 145; 204/265, 266; 417/379, 395

[56] References Cited

U.S. PATENT DOCUMENTS

| | | | |
|---|---|---|---|
| 4,350,477 | 9/1982 | Mazal | 417/384 |
| 4,687,423 | 8/1987 | Maget et al. | 417/379 |
| 5,062,834 | 11/1991 | Gross et al. | 604/143 |
| 5,090,963 | 2/1992 | Gross et al. | 604/132 |
| 5,242,406 | 9/1993 | Gross et al. | 604/141 X |
| 5,246,147 | 9/1993 | Gross | 222/394 |

FOREIGN PATENT DOCUMENTS

| | | |
|---|---|---|
| 0 209 677 | 1/1987 | European Pat. Off. |
| 0 494 042 | 7/1992 | European Pat. Off. |
| 1355521 | 2/1964 | France |
| 2 131 496 | 6/1984 | United Kingdom |
| 92 07614 | 5/1992 | WIPO |
| 93 23096 | 11/1993 | WIPO |

*Primary Examiner*—Kevin P. Shaver
*Attorney, Agent, or Firm*—Kathleen L. Maher

[57] ABSTRACT

A liquid material dispenser, for use, for example, in dispensing liquid medicine over an extended period of time, which includes a housing (10) enclosing a reservoir (12) for storing the liquid to be dispensed and having an outlet (14) through which the liquid is dispensed, and a connecting passageway (16) between the reservoir and the outlet. Located in the passageway is a diaphragm (18), one side of which defines a pumping chamber (20) and the other side of which defines a pressure control chamber (22). The diaphragm (18) is cyclically displaceable through a pumping stroke for pumping liquid through the outlet (14) and a drawing stroke for drawing liquid from the reservoir (12). Also located in the passageway (16) are a pair of valves (30, 33) which serve, during the drawing stroke, to cause the diaphragm (18) to draw liquid from the reservoir (12) into the pumping chamber (20), and during the pumping stroke, to cause the diaphragm (18) to pump liquid from the pumping chamber (20) through the outlet (14). An electrolytic cell (24) generates gas at suitable times for suitable durations and rates which is supplied to the pressure control chamber (22) to drive the pumping member (18) through the pumping stroke. A vent is used for venting the gas from the pressure control chamber (22) to the atmosphere to drive the pumping member (18) through the drawing stroke. The vent has an inlet vent opening (40) inside the pressure control chamber (22), with the opening (40) being caused to open to end the pumping stroke and to close after a portion of the gas has vented.

19 Claims, 3 Drawing Sheets

LIQUID MATERIAL DISPENSER AND VALVE

TECHNICAL FIELD

The present invention relates to liquid material dispensers, and a valve particularly suitable for use in such dispensers, and more particularly to dispensers for dispensing medicaments at small, precisely controlled rates.

BACKGROUND ART

The invention is especially useful where the liquid is driven from the dispenser by the force of gas generated at a suitable rate by an electrolytic cell. Examples of such systems are described in U.S. Pat. Nos. 5,062,834 and 5,090,963, and in our International Patent Publication WO 93/23096, which are incorporated by reference in their entirety for all purposes as if fully set forth herein.

In a variety of applications, including, but not limited to, drug delivery systems, it is required to dispense or deliver a liquid at a predetermined, precisely controlled rate. Electrolytic pumps, such as those described in the above-mentioned U.S. Patents, have been developed for this purpose. These pumps, however, generally include relatively large pumping chambers, and hence their pumping rates may be significantly influenced by pressure and temperature changes, particularly when the dispenser is used over long periods of time and/or under varying ambient conditions.

The electrolytic pump described in our International Patent Publication WO 93/23096 provides a liquid material dispenser or pump of a construction which can include a pumping chamber of relatively small volume so that the rate of delivery of the liquid is less sensitive to pressure and temperature variations.

However, the venting of the pressure control chamber is carried out through a slow acting vent which releases the gas from the pressure control chamber to the atmosphere to thereby drive the pumping member through the return stroke and draw liquid from the reservoir into the pumping chamber. Such a slow vent may at times become plugged, reducing the venting rate or interrupting it entirely. In addition, since the venting is carried out continuously at all times, it tends to reduce the efficiency of the pumping stroke by robbing the pumping chamber of some of its relatively high pressure gases when it is desired that those gases exert maximum force on the diaphragm to pump the liquid.

In addition, the device disclosed in our International Patent Publication WO 93/23096 uses a pair of one-way umbrella valves for controlling the flow of liquid from the reservoir to the outside of the device.

Furthermore, the device described in our International Patent Publication WO 93/23096 is designed so that gas production continues for a pre-determined period of time. The duration is selected so as to deliver the desired amount of liquid through the outlet. However, for a variety of reasons, including, but not limited to, partial plugging of the outlet or temperature and pressure variations, the amount of liquid delivered during a fixed period of time may vary.

There is thus a widely recognized need for, and it would be highly advantageous to have, an electrolytic pump along the lines described in our International Patent Publication WO 93/23096 but which would feature means for more efficiently venting the pressure control chamber and which would make use of more one-way valves, and which would have the ability to automatically discontinue the delivery of liquid when a fixed amount of liquid has been made to pass through the outlet.

DISCLOSURE OF INVENTION

According to the present invention there is provided a liquid material dispenser, comprising: (a) a housing including a reservoir for storing liquid to be dispensed, an outlet through which the liquid is dispensed, and a connecting passageway between said reservoir and said outlet; (b) a reciprocatable pumping member located in said passageway, one side of said pumping member defining a pumping chamber with said passageway, and the other side of said pumping member defining a pressure control chamber, said pumping member being cyclically displaceable through a pumping stroke for pumping liquid through said outlet and a drawing stroke for drawing liquid from said reservoir; (c) valve means in said passageway effective, during said drawing stroke, to cause the pumping member to draw liquid from said reservoir into said pumping chamber, and during said pumping stroke, to cause the pumping member to pump liquid from said pumping chamber through said outlet; (d) feeding means for feeding a gas at a preselected time and rate to said pressure control chamber to drive the pumping member through said pumping stroke; and (e) a vent mechanism for venting said gas from said pressure control chamber to the atmosphere to drive the pumping member through said drawing stroke, said vent mechanism having an inlet vent opening inside said pressure control chamber, said opening being caused to open to end said pumping stroke and to close after a portion of said gas has vented.

According to further features in preferred embodiments of the invention described below, the pumping member is a diaphragm and the vent mechanism includes a displaceable member connected to the pumping member, the displaceable member being formed with the inlet vent opening, the inlet vent opening being in communication with a vent conduit leading to the atmosphere, and further includes a blocking member slidably mounted over the displaceable member so that the blocking member can alternately block and uncover the inlet vent opening. The blocking member is biased in a direction away from the pumping member and the displaceable member includes means for preventing the blocking member from translating relative to the displaceable member beyond a certain location, thereby biasing the displaceable member, so that when the blocking member is at said location it blocks the inlet vent opening.

According to still further features in the described preferred embodiments, the biasing of the blocking member is achieved using at least one leaf spring connecting the walls of the pressure control chamber and the blocking member, one end of the leaf spring is held in a recession in the walls of the pressure control chamber and the other end of the leaf spring is held in a recession in the blocking member.

According to one embodiment of the present invention the vent conduit is connected to the pumping member.

According to another embodiment of the present invention the vent conduit is formed with the displaceable member and is slidable through a seal to the atmosphere.

According to further features in preferred embodiments, the feeding means includes an electrolytic cell which includes electrodes and electrolyte and which generates a gas at a rate substantially proportional to the electrical current passing through the electrolyte.

According to yet further features, the valve means comprises: (a) an upstream one-way valve in the passageway located between the reservoir and the pumping chamber and oriented such that during the drawing stroke the pumping member draws liquid from the reservoir to the pumping chamber; and (b) a downstream one-way valve in the passageway located between the pumping chamber and the outlet and oriented such that during the pumping stroke the pumping member pumps liquid from the pumping chamber through the outlet.

Also according to the present invention there is provided a one-way valve for controlling the flow of fluid through a passage, comprising: (a) means for fixing the position of the valve relative to the passageway; (b) a flexible member having a convex side in the direction of the flow and a concave side in the opposite direction; and (c) a slit in the flexible member such that when pressure is exerted upon the concave side the slit is made to open to allow the flow of fluid while when pressure is exerted on the convex side the slit is made to close and prevent the flow of fluid.

The present invention successfully addresses the shortcomings of the presently known configurations by providing a liquid dispenser which is actuated by closing an electrical circuit which activates an electrolytic cell so as to cause gas to be generated at a predetermined rate. When the pumping member has been sufficiently displaced, indicating the delivery through the device outlet of a substantially fixed amount of liquid, the vent opens automatically and, preferably, the gas generation is interrupted. The venting of the pressure control chamber brings about the drawing of additional liquid from the reservoir into the pumping chamber (the drawing stroke), where the liquid remains until gas is again generated so as to drive the diaphragm and thereby pump an additional aliquot of liquid out of the unit, during the pumping stroke.

The principles and operation of a liquid material dispenser and one-way valve according to the present invention may be better understood with reference to the drawings and the accompanying description.

BRIEF DESCRIPTION OF DRAWINGS

The invention is herein described, by way of example only, with reference to the accompanying drawings, wherein.

MODES FOR CARRYING OUT THE INVENTION

Figure 1:
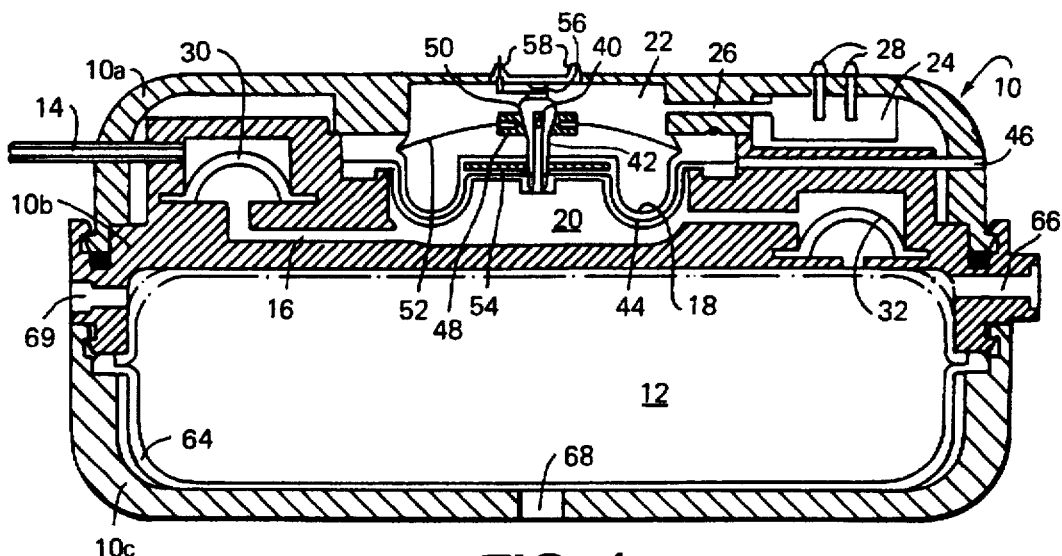
FIG. 1 is a cross-sectional view of one embodiment of a liquid material dispenser according to the present invention.

Referring now to the drawings, FIG. 1 illustrates a basic embodiment of a liquid material dispenser according to the present invention designed to deliver drugs at a slow, controlled and precise rate. Throughout the discussion which follows the dispenser is assumed to be used for the dispensing of medication, it being understood that such an application is merely illustrative of the many applications wherein it is desired to intermittently deliver a controlled amount of liquid at a relatively slow rate. The present invention is intended to cover all such applications and is not limited to medicinal applications.

The illustrated liquid dispenser according to the present invention has a housing 10 enclosing a reservoir 12 which contains the liquid to be dispensed. Housing 10 also includes an outlet 14 through which the liquid is dispensed, and a connecting passageway 16 between reservoir 12 and outlet 14. Passageway 16 includes an enlarged cavity which contains a movable, or reciprocatable, pumping member, preferably a diaphragm 18, which divides the enlarged cavity into a pumping chamber 20 and a pressure control chamber 22.

Diaphragm 18 serves as a reciprocating pumping member and is cyclically displaceable through a pumping stroke and a drawing stroke to effect the movement of liquid from reservoir 12 through outlet 14. As will be described in more detail below, during the drawing stroke, differential pressure across diaphragm 18 causes it to move in one direction (upwards in FIG. 1) as liquid moves from reservoir 12 to pumping chamber 20. During the pumping stroke, when the direction of differential pressure is reversed, diaphragm 18 is caused to move in the other direction (downwards in FIG. 1) causing liquid to move from pumping chamber 20 through passageway 16 to outlet 14.

The motion of diaphragm 18 during the pumping stroke is preferably brought about by an electrolytic cell 24 having a suitable electrolyte, such as sodium bicarbonate or, preferably, potassium acetate, located within housing 10 and in communication with pressure control chamber 22 via a bore 26. Also shown in FIG. 1 is a pair of electrodes 28 which are connected to a suitable electrical energy source (not shown) which may be housed either within or outside housing 10.

Electrolytic cell 24 may be of any known construction. Examples of possible configuration are described in U.S. Pat. Nos. 5,062,834 and 5,090,963, and in our International Patent Publication WO 93/23096.

Whenever appropriate, electrical energy is supplied to electrodes 28 at a preselected rate, bringing about electrolytic reactions which produce gases. The rate of gas production is related to the electrical current supplied to electrolytic cell 24 and the total amount of gases produced is related to the total electrical energy supplied to the cell. The produced gases flow from electrolytic cell 24 to pressure control chamber 22 through bore 26 to displace diaphragm 18 and thereby effect the pumping of liquid from pumping chamber 20 through the downstream portion of passageway 16 and out through outlet 14.

A downstream one-way valve 30 is anchored in that portion of passageway 16 between pumping chamber 20 and outlet 14 and is oriented such that during the pumping stroke of diaphragm 18, liquid is moved from pumping chamber 20 through outlet 14.

An upstream one-way valve 32 is anchored in that portion of passageway 16 between reservoir 12 and pumping chamber 20 and is oriented such that during the drawing stroke of diaphragm 18, liquid is drawn from reservoir 12 into pumping chamber 20.

One-way valves 30 and 32 can be of any suitable design, including the design described in our International Patent Publication WO 93/23096.

Figure 2:
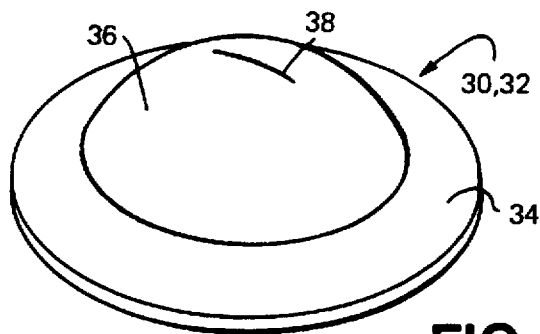
FIG. 2 is a one-way valve according to the present invention.

Preferably, as can best be seen in FIG. 2, one-way valves are of the unique design described below. It is to be noted that while the one-way valve described below is suitable for use in the context of a liquid material dispenser according to the present invention, it will be readily apparent to the reader that such valves may also be used in various other applications. It is intended that all such applications fall within the scope of the present invention.

Each of one-way valves 30 and 32 according to the present invention includes means for fixing the position of the valve relative to the passageway, for example, a rim 34 which is suitably connected to housing 10 (FIG. 1).

Connected to rim 34, preferably integrally formed with it, is a flexible member 36, preferably made of a suitable plastics or rubber. Flexible member has a convex side which is installed so as to face in the desired direction of the flow and a concave side which faces the opposite direction. Preferably, flexible member 36 is hemispherical, or partly spherical, in shape. Flexible member 36 features near its centre a slit 38 of suitable length and shape.

Thus, when diaphragm 18 pushes downward, pressure is exerted on the concave side of downstream valve 30 and on the convex side of upstream valve 32. The exertion of pressure on the concave side of downstream valve 30 tends to bend flexible member 36 of valve 30 downstream in the direction of outlet 14. The bending tends to cause the portions of flexible member 36 of valve 30 which border on slit 38 to separate, thereby allowing liquid to flow downstream through the formed opening.

At the same time, the exertion of pressure on the convex side of upstream valve 32 tends to push flexible member 36 of valve 32 upstream in the direction of reservoir 12. This tends to cause the portions of flexible member 36 of valve 32 which border on slit 38 to come together, thereby sealing the opening and preventing liquid from flowing upstream through valve 32.

Similarly, when the pressure in pressure control chamber 22 is reduced, as will be described below, diaphragm 18 moves upwards and pressure is reduced in pumping chamber 20, on the concave side of downstream valve 30 and on the convex side of upstream valve 32. The reduction in pressure allows liquid to move through the upstream valve 32 and at the same time tightly closes downstream valve 30 to prevent any liquid from entering the device from the outside through outlet 14.

A liquid material dispenser according to the present invention further features a vent mechanism for venting gases created by electrolytic cell 24 from pressure control chamber 22 to the atmosphere. The venting drops the pressure in pressure control chamber 22 and causes diaphragm 18 to move so as to draw liquid from reservoir 12 into pumping chamber 20, as described above.

The vent mechanism includes an inlet vent opening 40 located in pressure control chamber 22. As will be described below in more detail, inlet vent opening 40 is caused to alternately open to end the pumping stroke and vent pressure control chamber 22 and to close after a portion of the gases has vented.

The vent mechanism includes a displaceable member 42 which is connected to diaphragm 18. Displaceable member 42 is formed with inlet vent opening 40 which is in communication with a flexible vent conduit 44 connected to diaphragm 18 and leading to the atmosphere through a fixed vent conduit 46 formed in housing 10. The communication between inlet vent opening 40 and flexible vent conduit 44 is preferably effected through a hollow portion of displaceable member 42.

The vent mechanism further includes a blocking member 48 which is slidably mounted over displaceable member 42 so that blocking member 48 can alternately block and uncover inlet vent opening 40 as described in more detail below.

Preferably, displaceable member 42 includes a section which is frusto-conical in shape and blocking member 48 is annular with an inner diameter which is somewhat bigger than the outside diameter of the smallest diameter portion of the frusto-conical segment of displaceable member 42. Preferably also, displaceable member 42 features means for preventing blocking member 48 from translating relative to said displaceable member beyond a certain location, such as a ledge 50, adjoining the largest diameter portion of the frusto-conical segment of displaceable member 42, and having an outside diameter which is somewhat larger than the inner diameter of blocking member 48, thereby preventing blocking member from sliding past ledge 50. The function of ledge 50 can also be achieved by other means, such as the horizontal portion 51 of displaceable member 42 shown in FIG. 3.

Blocking member 48 is normally biased in a direction away from diaphragm 18 (upwards in FIG. 1). Thus, whenever blocking member 48 abuts against ledge 50, displaceable member 42 is also biased in the same direction.

The relative location and dimensions of displaceable member 42, blocking member 48 and inlet vent opening 40 are such that whenever blocking member 48 abuts against ledge 50, inlet vent opening 40 is blocked, or closed, thereby preventing gases from leaving pressure control chamber 22.

The biasing of blocking member 48, and therefore of displaceable member 42, as described above, is preferably achieved through use of one or more biasing springs, preferably one or more leaf springs 52, one end of each of which touches, or connects to, a wall of pressure control chamber 22 while the other end touches, or connects to, blocking member 48.

Preferably, the ends of leaf springs 52 fit into recessions in the walls of pressure control chamber 22 and blocking member 48.

The length of leaf spring 52 is such that when the vent mechanism is in its neutral position (shown in FIGS. 1 and 3), leaf spring 52 is slightly bent so as to produce the upward bias on blocking member 48 and displaceable member 42, as described above.

In operation, electrical energy is supplied at a suitable rate to electrolytic cell 24 causing it to generate gases which enter pressure control chamber 22 and raise its pressure. The increased pressure causes diaphragm 18 to move downward so as to push liquid through outlet 14 as described above. Since displaceable member 42 is connected to diaphragm 18, a force is exerted on displaceable member 42 to move downward. This force is at first counteracted by the upward biasing force exerted by leaf spring 52.

As the downward movement of diaphragm 18 continues, the downward force on displaceable member 42 increases, eventually equalling and overcoming the biasing force. At this point, leaf springs 52 instantaneously straighten and then bend rapidly in the downward direction, causing blocking member 48 to slide downward relative to displaceable member 42, so that blocking member abuts against abutting portion 54 of displaceable member 42. The relative movement of blocking member 48 and displaceable member 42 exposes inlet vent opening 40. Since the pressure in pressure control chamber 22 is larger than in the atmosphere outside the dispenser, gases flow quickly through inlet vent opening 40, flexible vent conduit 44 and fixed vent conduit 46 and escape to the outside of the dispenser.

The venting of the gases brings about a rapid pressure drop in pressure control chamber 22 causing the pressure in pressure control chamber 22 to rapidly fall from a pressure above that in pumping chamber 20 to a pressure below the pressure in pumping chamber 20. The resulting pressure differential pushes displaceable member 42 rapidly upward. As displaceable member 42 moves upward, abutting portion 54 of displaceable member 42 pushes blocking member 48 upward past the anchoring point of leaf spring 52 in the wall of pressure control chamber 22 which causes leaf spring 52 to bend upwards, thereby upwardly biasing blocking member 48, and displaceable member 42, as described above, and causing blocking member 48 to block, or close, inlet vent opening 40, thereby terminating the venting of gases from pressure control chamber 22.

The length and strength of leaf spring 52, as well as the other components of the vent mechanism, are designed to actuate as described above so that a substantially fixed quantity of liquid is dispensed during each pumping stroke.

Preferably, a dispenser according to the present invention also includes a pair of electrical contacts 56 which are arranged so that when displaceable member 42 is in its upwardly biased position contacts 56 are touching each other, while when displaceable member 42 is displaced downward during venting, as described above, contacts 56 are slightly separated from each other, through, for example, a slight downward bias on the lower of the two contacts 56.

Contacts 56 are electrically connected to taps 58 which are, in turn, connected to a suitable electrical circuit (not shown) which senses the moment of separation of contacts 56 and is capable of using the information to cut off electrical energy to electrolytic cell 24 so that no gases are generated while pressure control chamber 22 is vented and during the period from the completion of the venting until the initiation of the next pumping stroke.

Figure 3:
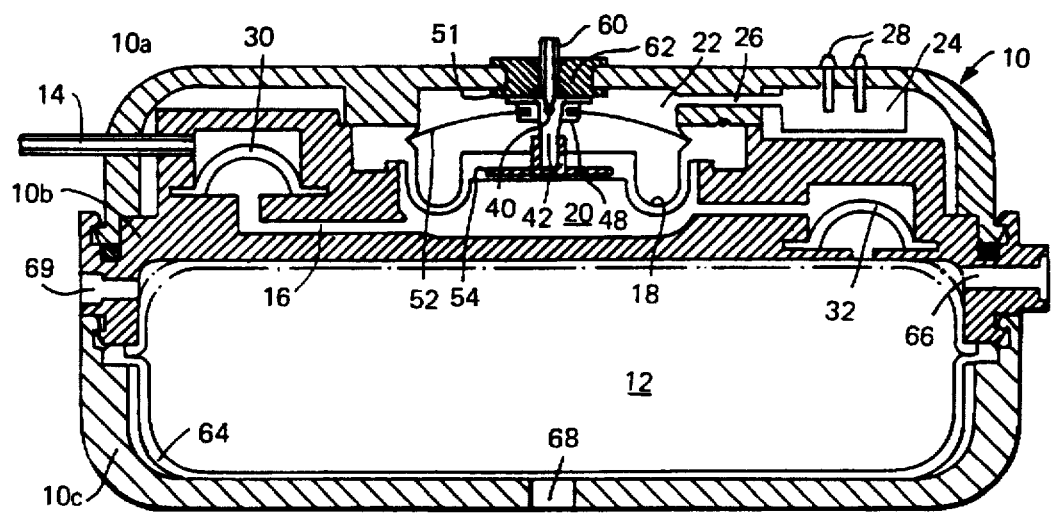
FIG. 3 is a cross-sectional view of a second embodiment of a liquid material dispenser according to the present invention.

Shown in FIG. 3 is a second embodiment according to the present invention, wherein inlet vent opening 40 does not communicate with a flexible vent conduit as in the embodiment of FIG. 1, but rather communicates directly with a vent conduit 60 which is connected to, or preferably, integrally formed with, displaceable member 42. Vent conduit 60 is sufficiently long to extend through housing 10 to the atmosphere. A suitable seal 62 allows vent conduit 60 to slide up and down yet seals pressure control chamber 22 so that no gases can escape except through vent conduit 60.

As will be readily apparent to the reader, the embodiment shown in FIG. 3 can include contacts 56 and taps 58 as shown in the embodiment of FIG. 1. These have been omitted from FIG. 3 to enhance clarity.

Housing 10, reservoir 12 and/or diaphragm 18 may be made of any suitable configuration, e.g., circular or rectangular in cross-section, and may be made of any suitable materials.

For ease in assembly and disassembly of the illustrated dispenser, housing 10 is made of a plurality of sections—a top section 10a, a middle section 10b and a bottom section 10c. Top section 10a and middle section 10b clamp together to define between them pumping chamber 20 and pressure control chamber 22 and further form a volume which serves to house electrolytic cell 24.

Middle section 10b and bottom section 10c clamp together to define between them a cavity which includes reservoir 12 and to hold in place a rolling diaphragm 64, which is flexible and preferably made of silicon rubber. It will be seen that reservoir 12 is defined by middle section 10b and rolling diaphragm 64. Rolling diaphragm 64 is shown in FIGS. 1 and 3 as it would appear when reservoir 12 is full of liquid. Shown in broken lines in FIG. 3 is rolling diaphragm 64 as it would appear when reservoir 12 is empty. Diaphragm 18 and a reservoir vent opening 68 permit reservoir 12 to expand and contract according to the amount of liquid material contained in reservoir 12 as rolling membrane 64 moves.

Middle section 10b carries an injection plug 66 for filling the reservoir by injection via a syringe needle (not shown). Middle section 10b also includes an injection vent 69 which allows air to escape during the injection of liquid into reservoir 12.

The rims 34 of valves 30 and 32 are secured in openings formed in middle section 10b.

The illustrated dispenser operates as follows. Reservoir 12 is filled with liquid using a syringe (not shown) which pierces injection plug 66. Injection is continued until the injected liquid begins to exit from outlet 14, indicating that reservoir 12, connecting passageway 16 and pumping chamber 20 are all completely filled with the liquid.

The rate of delivery of the liquid from reservoir 12 to outlet 14 is controlled by an electrical control circuit (not shown) which controls the energizing of electrolytic cell 24 through electrodes 28. During the interval when electrodes 28 are energized, electrolytic cell 24 generates a gas or gases which are fed via bore 26 to pressure control chamber 22. These gases displace diaphragm 18 downward, thereby stressing diaphragm 18 and contracting pumping chamber 20. This contraction of pumping chamber 20 applies a pressure via passageway 16 to close upstream valve 32 and open downstream valve 30. Accordingly, liquid from pumping chamber 20 is pumped via valve 30 through outlet 14 while electrolytic cell 24 produces gas at a rate which is related to the magnitude of electrical current supplied to it.

As described above, at a certain point in the pumping stroke, blocking member 48 moves downward relative to displaceable member 42 exposing inlet vent opening 40 and venting pressure control chamber 22, and simultaneously interrupting the generation of gases by electrolytic cell 24.

Following venting, blocking member 48 and displaceable member 42, as well as the other components of the vent mechanism, return to their rest position (as shown in FIGS. 1 and 3) with pumping chamber 20 having been refilled with liquid drawn from reservoir 12.

When electrical current is again applied to electrolytic cell 24 diaphragm 18 will again be driven through a pumping stroke and will pump the liquid through valve 30 and out through outlet 14.

Figure 4:
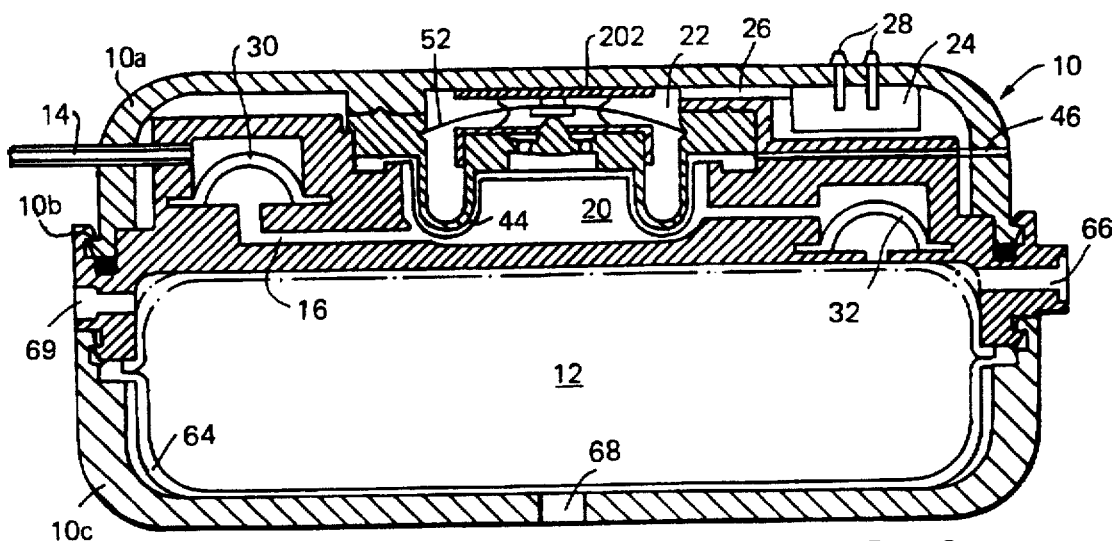
FIG. 4 is a cross-sectional view of a third embodiment of a liquid material dispenser according to the present invention.
Figure 5:
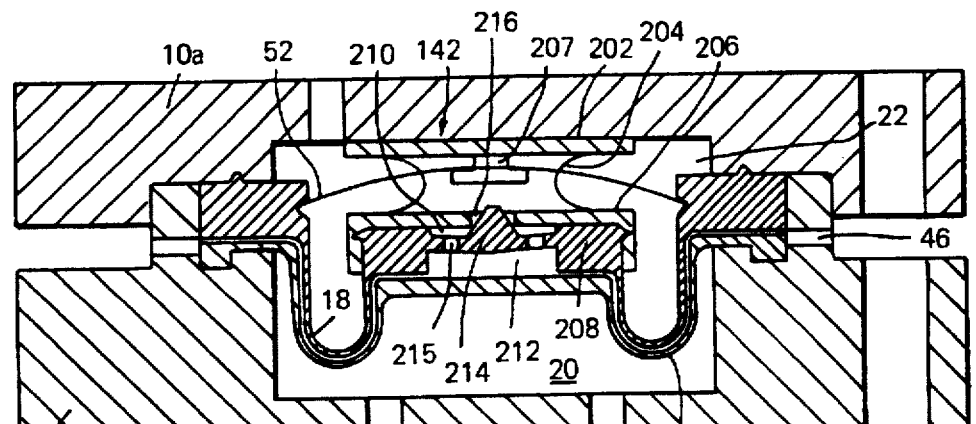
FIG. 5 is an enlarged view of the top central portion of the dispenser of FIG. 4 with the leaf spring in its top position.
Figure 6:
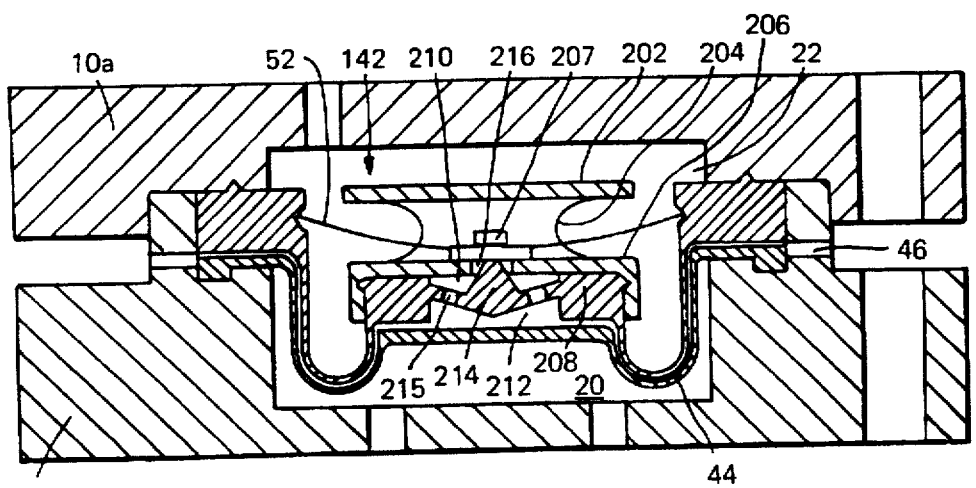
FIG. 6 is an enlarged view of the toll central portion of the dispenser of FIG. 4 with the leaf spring in its bottom position.

Shown in FIGS. 4–6 is a third embodiment according to the present invention, which is generally the same as the embodiments depicted in FIGS. 1 and 3 except for variations in the mechanism used to vent pressure control chamber 22 which are described below.

A liquid material dispenser according to the embodiment shown in FIGS. 4–6 features a somewhat different vent mechanism for venting gases created by electrolytic cell 24 from pressure control chamber 22 to the atmosphere. The venting drops the pressure in pressure control chamber 22 and causes diaphragm 18 to move so as to draw liquid from reservoir 12 into pumping chamber 20, as described above.

The vent mechanism shown in FIG. 4, and in more detail, in the enlarged views of FIGS. 5 and 6, includes a displaceable member 142 which is connected to diaphragm 18 and which is made up of a number of portions.

Displaceable member 142 includes an upper member 202 which is able to lie flat against the top inner wall of pressure control chamber 22 when the pressure control chamber is not being vented. Upper member 202 is rigidly connected to the rest of displaceable member 142 via a suitable connecting member 204, which is preferably in the form of a series of ribs extending downward from upper member 202 to a central member 206.

Extending through or between connecting member 204, through a slot (not shown) is leaf spring 52 which also passes through an impact member 207 which is not connected to displaceable member 142 and is free to move between upper member 202 and central member 206 of displaceable member 142. Leaf spring 52 and impact member 207 are located such that the downward motion of upper member 202 causes the downward motion of impact member 207 which in turn, causes the same downward motion of leaf spring 52.

Central member 206 is connected to a lower member 208 and together with it forms a secondary chamber. The secondary chamber is split into an upper secondary chamber 210 and a lower secondary chamber 212 by a displaceable plug 214 which is anchored to, or forms a portion of lower member 208.

Displaceable plug 214 features one or more suitably located bores 215 which serve to continuously connect upper secondary chamber 210 and lower secondary chamber 212. The size, shape and movement of displaceable plug 214 are designed so that it can alternately extend through an opening 216 in central member 206 so as to close off or isolate upper secondary chamber 210, and therefore also lower secondary chamber 212 from pressure control chamber 22, or retreat downward from opening 216 so as to put secondary chamber 210, and therefore also lower secondary chamber 212, in communication with pressure control chamber 22.

Lower secondary chamber 212 is in continuous communication with flexible vent conduit 44 connected to diaphragm 18 and leading to the atmosphere through a fixed vent conduit 46 formed in housing 10.

The length of leaf spring 52 is such that when the vent mechanism is in its neutral position (shown in FIG. 5), leaf spring 52 is slightly bent so as to produce the upward bias on impact member 207.

In operation, electrical energy is supplied at a suitable rate to electrolytic cell 24 causing it to generate gases which enter pressure control chamber 22 and raise its pressure. The increased pressure causes diaphragm 18 to move downward so as to push liquid through outlet 14 as described above. Since displaceable member 142 is connected to diaphragm 18, force is exerted on displaceable member 142, moving it downward. The downward movement of displaceable member 142 also serves to move impact member 207 and leaf spring 52 downward.

As the downward movement continues, downward force on leaf spring 52 is increased. Eventually the downward force on leaf spring 52 exceeds its upwardly directed biasing force. At this point, leaf spring 52 instantaneously straightens and then bends rapidly in the downward direction, causing impact member 207 to move rapidly downward and impact displaceable plug 214. The impact causes displaceable plug 214 to move downward, which opens the previously closed opening 216, putting pressure control chamber 22 in communication with upper secondary chamber 210 (and therefore with lower secondary chamber 212 and flexible vent conduit 44 and fixed vent conduit 46) and allowing the gases in pressure control chamber 22 to be released outside the device. Since the pressure in pressure control chamber 22 is higher than in the atmosphere outside the dispenser, gases quickly escape to the outside of the dispenser.

The venting of the gases brings about a rapid pressure drop in pressure control chamber 22 causing the pressure in pressure control chamber 22 to rapidly fall from a pressure above that in pumping chamber 20 to a pressure below the pressure in pumping chamber 20. The resulting pressure differential pushes displaceable member 142 rapidly upward. As displaceable member 142 moves upwards eventually leaf spring 52 bends upward to push impact member 207 upward and away from displaceable plug 214, allowing displaceable plug 214 to rise so as to once again close opening 216 between pressure control chamber 22 and the outside of the dispenser.

BEST MODE FOR CARRYING OUT THE INVENTION

Figure 7:
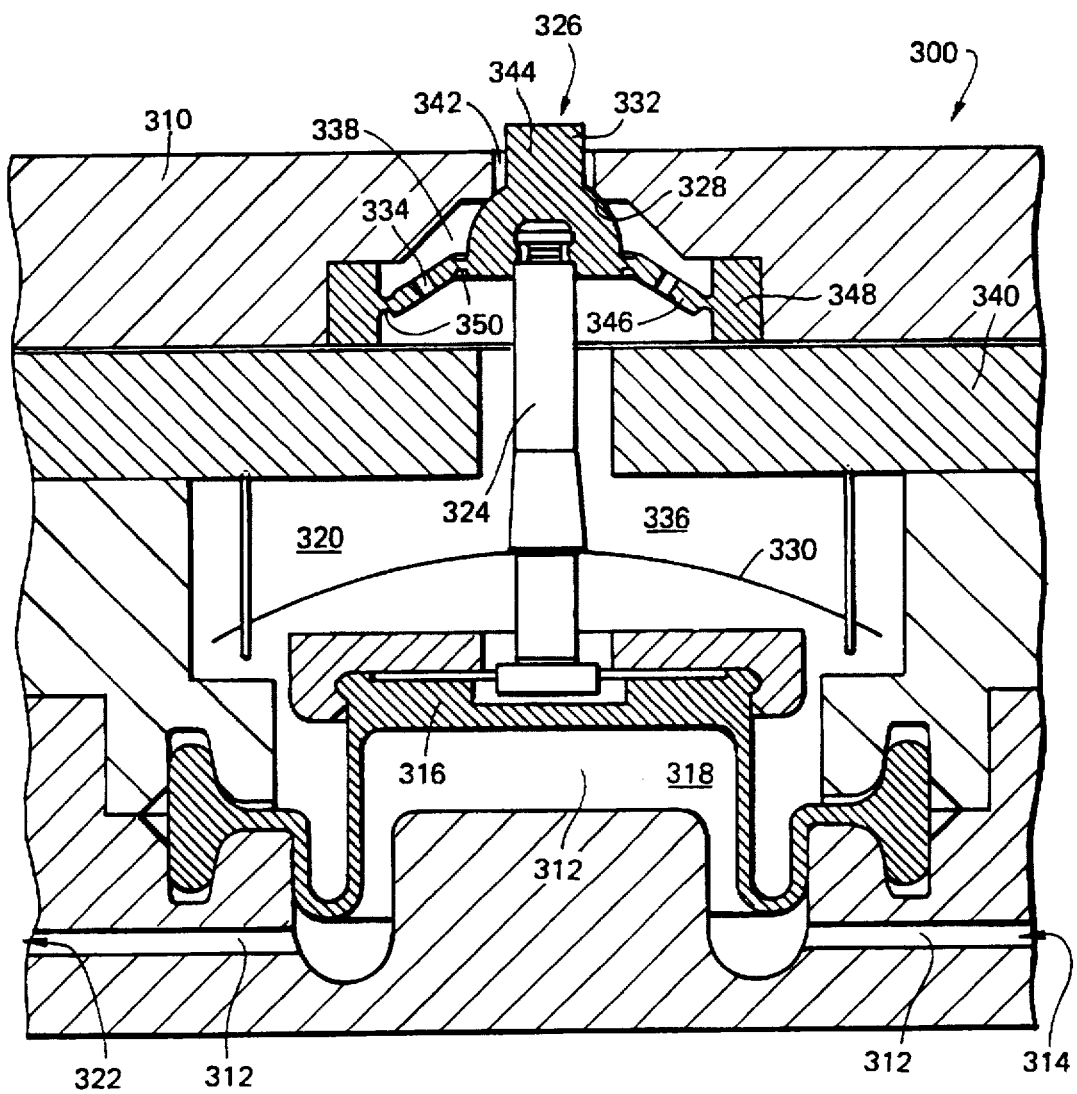
FIG. 7 is an enlarged cross-sectional view of the top central portion of a fourth embodiment of a liquid material dispenser according to the invention.

Shown in FIG. 7 is a fourth and presently preferred embodiment according to the present invention, which is generally the same as the embodiments depicted in FIGS. 1, 3 and 4-6 except for variations in the mechanism used to vent pressure control chamber 22, as described below. Accordingly, FIG. 7 shows an enlarged detail of the venting mechanism.

Thus, in FIG. 7 there is illustrated, generally at 300, a detail of a liquid material dispenser according to the present invention. The dispenser has a housing 310 including a reservoir (not shown) which contains the liquid to be dispensed and including an outlet (not shown) through which the liquid is dispensed. As with the embodiments illustrated in FIGS. 1, 3 and 4-6, the liquid travels from the reservoir to the outlet via a passageway 312 having an upstream one-way valve and a downstream one-way valve (not shown). Thus, liquid coming from the reservoir and upstream valve through passageway 312 enters the illustrated portion of the dispenser via the part of passageway 312 indicated at 314 in FIG. 7. Within passageway 312 there is located a diaphragm 316 defining on one side thereof, with passageway 312, a pumping chamber 318 and, on the other side thereof, a pressure control chamber 320. The diaphragm 316 is cyclically displaceable so as to draw liquid into the pumping chamber 318 from the reservoir and upstream valve and to pump liquid from pumping chamber 318 along connecting passageway 312 towards the downstream valve and the outlet in the direction indicated at 322.

Diaphragm 316 is connected via a connecting rod 324 to a vent mechanism, indicated generally at 326, having an inlet vent opening 328. A leaf spring 330 is secured within pressure control chamber 320 and is connected to connecting rod 324. When the vent mechanism is in its neutral position, leaf spring 330 is slightly bent so as to produce an upward bias on connecting rod 324. Inlet vent opening 328 is defined between a seal member 332 and housing 310. Seal member 332 is connected via connecting rod 324 to diaphragm 316.

Pressure control chamber 320 extends front diaphragm 316 up to inlet vent opening 328. One or more gaps 334 in seal member 332 allow communication between lower part 336 and upper part 338 of pressure control chamber 320.

In operation, gas is generated within pressure control chamber 320 by an electrolytic cell 340, causing diaphragm 316 to be displaced downwards through the pumping stroke. Leaf spring 330 initially opposes this downward force but, as in the other embodiments, the upward bias provided by spring 330 is eventually overcome, and the spring straightens and then snaps downwards when it reaches the horizontal position. This snapping action causes seal member 332 to snap downwards, causing inlet vent opening 328 to open and thereby allowing the pressurised gas within pressure control chamber 320 to escape via inlet vent opening 328 through a vent outlet 342.

Seal member 332 comprises a central portion 344, a frusto-conical section 346 within which gap 334 is located, and an anchor section 348 holding the seal member 332 in position. Hinges 350 allow central portion 344 to move downwards and upwards in relation to anchor section 348, which movements respectively open and seal inlet vent opening 328 inside the upper part 338 of pressure control chamber 320.

The escape of the pressurised gas allows leaf spring 330 to relax, whereby diaphragm 316, connecting rod 324 and seal member 332 move upwards, until inlet vent opening 328 is resealed. The upward movement of diaphragm 316 draws liquid from the reservoir through the upstream valve and via the connecting passageway at 314 into pumping chamber 318. Thus, pumping chamber 318 is refilled and inlet vent opening 328 is resealed allowing the pumping stroke to begin again.

It will be appreciated that the illustrated dispenser does not hold large volumes of gases over extended periods, and therefore is not significantly sensitive to temperature and pressure fluctuations. In addition, it will be noted that a dispenser according to the present invention tends to deliver substantially the same amount of liquid in each successive pumping stroke. The illustrated dispenser may therefore be used for intermittently dispensing precisely set amounts of liquids at precisely controlled rates.

I claim:

1. A liquid material dispenser, comprising:
   (a) a housing including a reservoir for storing liquid to be dispensed, an outlet through which the liquid is dispensed, and a connecting passageway between said reservoir and said outlet;
   (b) a reciprocatable pumping member located in said passageway, one side of said pumping member defining a pumping chamber with said passageway, and the other side of said pumping member defining a pressure control chamber, said pumping member being cyclically displaceable through a pumping stroke for pumping liquid through said outlet and a drawing stroke for drawing liquid from said reservoir;
   (c) valve means in said passageway effective, during said drawing stroke, to cause the pumping member to draw liquid from said reservoir into said pumping chamber, and during said pumping stroke, to cause the pumping member to pump liquid from said pumping chamber through said outlet;
   (d) feeding means for feeding a gas at a preselected time and rate to said pressure control chamber to drive the pumping member through said pumping stroke; and
   (e) a vent mechanism for venting said gas from said pressure control chamber to the atmosphere to drive the pumping member through said drawing stroke, said vent mechanism including: an inlet vent opening providing communication between the pressure control chamber and the atmosphere; said opening being caused to open to end said pumping stroke and to close after a portion of said gas has vented, wherein said vent mechanism includes a displaceable member connected to said pumping member, such that the opening and sealing of the vent opening occurs as a result of the movement of the displaceable member under the action of the pumping member.

2. A dispenser as claimed in claim 1, wherein said displaceable member is formed with said inlet vent opening, and said inlet vent opening is in communication with a vent conduit leading to the atmosphere.

3. A dispenser as claimed in claim 2, wherein said vent mechanism further includes a blocking member slidably mounted over said displaceable member so that said blocking member can alternately block and uncover said inlet vent opening.

4. A dispenser as claimed in claim 3, wherein said blocking member is biased in a direction away from said pumping member and wherein said displaceable member includes means for preventing said blocking member from translating relative to said displaceable member beyond a certain location, thereby biasing said displaceable member, so that when said blocking member is at said location it blocks said inlet vent opening.

5. A dispenser as claimed in claim 4, wherein said means for preventing said blocking member from translating relative to said displaceable member beyond a certain location includes a ledge formed with said displaceable member having a transverse dimension larger than the transverse dimension of the opening of said blocking member.

6. A dispenser as claimed in claim 4, wherein said biasing of said blocking member is achieved using at least one leaf spring connecting the walls of said pressure control chamber and said blocking member.

7. A dispenser as claimed in claim 6, wherein one end of said leaf spring is held in a recession in the walls of said pressure control chamber and the other end of said leaf spring is held in a recession in said blocking member.

8. A dispenser as claimed in claim 2, wherein said vent conduit is connected to said pumping member.

9. A dispenser as claimed in claim 8, further comprising a pair of electrical contacts arranged so that when said displaceable member is in its biased position said contacts make contact with each other.

10. A dispenser as claimed in claim 2, wherein said vent conduit is formed with said displaceable member and is slidable through a seal to the atmosphere.

11. A dispenser as claimed in claim 1, wherein said feeding means includes an electrolytic cell which includes electrodes and electrolyte and which generates a gas at a rate substantially proportional to the electrical current passing through said electrolyte.

12. A dispenser as claimed in claim 11, further comprising a pair of electrical contacts arranged so that when said displaceable member is in its biased position said contacts make contact with each other to close an electrical circuit, which circuit controls said gas generation.

13. A dispenser as claimed in claim 11, wherein said electrolytic cell communicates with said pressure control chamber.

14. A dispenser as claimed in claim 1, wherein said pumping member is a diaphragm.

15. A dispenser as claimed in claim 1, wherein said vent mechanism further comprises a seal member anchored to the housing, said seal member having a portion which is movable relative to the housing to open or seal the vent opening, and said displaceable member being connected both to the pumping member and to said portion of the seal member.

16. A dispenser as claimed in claim 1, wherein said housing includes a top section, a middle section and a bottom section, said pressure control chamber and said pumping chamber being defined by said top and said middle sections.

17. A dispenser as claimed in claim 1, wherein said housing includes a top section, a middle section and a bottom section, said reservoir being defined by said middle and bottom sections, said middle section including an injection plug and said bottom section including a reservoir vent opening.

18. A dispenser as claimed in claim 1, wherein said valve means comprises:

(a) an upstream one-way valve in said passageway located between said reservoir and said pumping chamber and oriented such that during said drawing stroke the pumping member draws liquid from said reservoir to said pumping chamber; and (b) a downstream one-way valve in said passageway located between said pumping chamber and said outlet and oriented such that during said pumping stroke the pumping member pumps liquid from said pumping chamber through said outlet.

19. A dispenser as claimed in claim 18, wherein said upstream and downstream valves each include means for fixing the position of said valves relative to said passageway and further include a flexible member having a convex side in the direction of the flow and a concave side in the opposite direction, said flexible member having a slit such that when pressure is exerted upon said concave side said slit is made to open to allow the flow of fluid while when pressure is exerted on the convex side said slit is made to close and prevent the flow of fluid.

* * * * *